United States Patent
Agrawal et al.

(10) Patent No.: US 6,323,364 B1
(45) Date of Patent: Nov. 27, 2001

(54) RHODIUM/INORGANIC IODIDE CATALYST SYSTEM FOR METHANOL CARBONYLATION PROCESS WITH IMPROVED IMPURITY PROFILE

(75) Inventors: Pramod Agrawal, Bay City; Hung-Cheun Cheung, Corpus Christi; Darrell A. Fisher, Houston; Valerie Santillan; Mark O. Scates, both of Friendswood; Elaine C. Sibrel; G. Paul Torrence, both of Corpus Christi, all of TX (US)

(73) Assignee: Celanese International Corporation

( * ) Notice: Subject to any disclaimer, the term of this patent is extended or adjusted under 35 U.S.C. 154(b) by 0 days.

(21) Appl. No.: 09/386,561

(22) Filed: Aug. 31, 1999

(51) Int. Cl.$^7$ .................................................. C07C 51/12
(52) U.S. Cl. ........................ 562/519; 562/517; 562/607
(58) Field of Search .................... 562/519, 607, 562/517

(56) References Cited

U.S. PATENT DOCUMENTS

| | | | |
|---|---|---|---|
| 3,769,329 | 10/1973 | Paulik et al. | 260/488 |
| 5,001,259 | 3/1991 | Smith et al. | 562/519 |
| 5,026,908 | 6/1991 | Smith et al. | 562/519 |
| 5,144,068 | 9/1992 | Smith et al. | 562/519 |
| 5,817,869 | * 10/1998 | Hinnenkamp et al. | |
| 6,031,129 | * 2/2000 | Hinnenkamp et al. | |

FOREIGN PATENT DOCUMENTS

| | | | |
|---|---|---|---|
| 0 055 618 | 12/1981 | (EP) | C07C/51/12 |
| 0 161 874 B2 | 5/1985 | (EP) | C07C/53/08 |

OTHER PUBLICATIONS

Hjortkjaer and Jensen [Ind. Eng. Chem., Prod Res. Dev. 16, 281–285 (1977)].
Ullman's Encyclopedia of Industrial Chemistry, "Acetic Acid", vol. A1, p. 56, 5th ed.

* cited by examiner

*Primary Examiner*—Paul J. Killos
*Assistant Examiner*—Robert W. Deemie
(74) *Attorney, Agent, or Firm*—M. Susan Spiering

(57) ABSTRACT

The method of the present invention provides an improvement upon prior art methanol carbonylation methods which substantially reduces the production of carbonyl impurities.

The production of carbonyl impurities, particularly acetaldehyde, crotonaldehyde, and 2-ethyl crotonaldehyde, in methanol carbonylation reactions has been found to decrease by maintaining less than about 4.5 wt % methyl iodide in the reaction medium during the course of the reaction.

15 Claims, No Drawings

RHODIUM/INORGANIC IODIDE CATALYST SYSTEM FOR METHANOL CARBONYLATION PROCESS WITH IMPROVED IMPURITY PROFILE

BACKGROUND OF THE INVENTION

1. Field of the Invention

The present invention is directed to an improvement in the process for the carbonylation of methanol to produce acetic acid. More specifically, the improved method of the present invention reduces the formation of carbonyl impurities in the carbonylation reaction by way of conducting the reaction with low amounts of methyl iodide.

2. The Related Art

There are a number of currently-employed processes for producing acetic acid. One of the most useful commercially is the carbonylation of methanol with carbon monoxide, now known as the Monsanto process. This methanol carbonylation process, as exemplified by U.S. Pat. No. 3,769,329 ("the '329 patent") issued to Paulik and assigned to the Monsanto Company, is the process used to produce the majority of the acetic acid commercially worldwide.

The process utilizes a catalyst comprised of rhodium, either dissolved or otherwise dispersed in the liquid reaction medium and a halogen-containing catalyst promoter as exemplified by, preferably, methyl iodide. Rhodium can be introduced into the reaction system in any of many forms, and it is not relevant, if indeed it is possible, to identify the exact nature of the rhodium moiety within the active catalyst complex. Likewise, the nature of the halide promoter is not critical. The '329 patent discloses a very large number of suitable halide promoters, most of which are organic iodides. Most typically and usefully, the reaction is conducted with the catalyst being dissolved in a liquid reaction medium through which carbon monoxide gas is continuously bubbled.

The '329 patent indicates that the liquid reaction medium can be any solvent compatible with the catalyst system and that it may comprise, for example, the pure alcohol which is being reacted, or mixtures thereof with the desired carboxylic acid end product and/or esters of these two compounds. The preferred solvent and liquid reaction medium for the process is the desired carboxylic acid itself, i.e., acetic acid when methanol is being carbonylated to produce acetic acid. The reaction medium is preferably comprised of rhodium, methanol, methyl iodide, methyl acetate, acetic acid, and water.

Importantly, the '329 patent indicates that a substantial quantity of water should be present in the reaction mixture in order to attain a satisfactorily high reaction rate. Furthermore, the patent indicates that reducing the water content of the reaction medium leads to the production of ester product as opposed to carboxylic acid. Indeed, European Patent Application 055,618, also assigned to Monsanto Company, indicates that typically about 14–15 weight percent (wt %) water is present in the reaction medium of a typical acetic acid plant using this technology. Likewise, Hjortkjaer and Jensen [*Ind. Eng. Chem., Prod Res. Dev.* 16, 281–285 (1977)] have shown that increasing the water from 0 to 14 wt % water increases the reaction rate of methanol carbonylation.

European Patent Application EP 055, 618 indicates that rhodium tends to precipitate out of the reaction medium. This tendency is most pronounced during the course of distillation operations to separate the product acetic acid from the reaction medium when the carbon is monoxide content of the catalyst system is reduced. The tendency for rhodium to precipitate out of the reaction medium increases as the water content of the reaction medium is decreased. Accordingly, based on the teachings of the '329 patent and European Patent Application EP 055,618, a substantial quantity of water is required in the reaction medium in order to combat the tendency for rhodium to precipitate, i.e., to maintain catalyst stability.

Preferably, commercial acetic acid is anhydrous or nearly anhydrous ("glacial"). Recovering acetic acid in anhydrous or nearly anhydrous form from a reaction medium comprising 14–15 wt % water, i.e., separating the acetic acid from the water, involves substantial expenditure of energy in distillation and/or additional processing steps.

Improvements have been made to the basic Monsanto process exemplified by the '329 patent. Of interest for the purposes of the present invention are those improvements which have allowed the operation of the process at water concentrations below 14 wt %. Commonly assigned U.S. Pat. Nos. 5,001,259; 5,026,908; 5,144,068; and European Patent No. 161,874B2 all provide improved methods of carbonylating methanol wherein the water content is maintained substantially below 14 wt %. As disclosed in those patents, acetic acid is produced from methanol in a reaction medium comprising methyl acetate, methyl halide, especially methyl iodide, and rhodium present in a catalytically effective concentration. The patents also disclose the unexpected discovery that catalyst stability and the productivity of the carbonylation reactor can be maintained at surprisingly high levels, even at very low water concentrations, i.e., 4 wt % or less, in the reaction medium (despite the general industry practice of maintaining approximately 14–15 wt % water) by maintaining in the reaction medium, along with a catalytically effective amount of rhodium, at least a finite concentration of water, methyl acetate and methyl iodide, and a specified concentration of iodide ions over and above the iodide content which is present as methyl iodide or other organic iodide. The iodide ion is present as a simple salt, with lithium iodide being preferred. These patents teach that the concentration of methyl acetate and iodide salts are significant parameters affecting the rate of carbonylation of methanol to produce acetic acid especially at low water concentrations.

In general, U.S. Pat. No. 5,144,068 and the related patents noted above teach that high levels of methyl iodide are desirable. Note FIGS. 4, 16 and 22 of the '068 patent, as well as Table 2, at column 9, lines 41–54 of the '068 patent.

By using relatively high concentrations of methyl iodide, methyl acetate and an iodide salt, one obtains a surprising degree of catalyst stability and reactor productivity even when the reaction medium contains extremely low water concentrations. Thus, these patented processes allow the production of acetic acid at lower water concentrations than previously known in the prior art. U.S. Pat. Nos. 5,001,259; 5,026,908; and 5,144,068 and European Patent No. 0 161 874 B2 are herein incorporated by reference.

Nonetheless, as the methanol carbonylation process has been practiced at increasingly lower water concentrations other problems have been found to have arisen. Specifically, operating at this new lower water regime has exacerbated certain impurities in the product acetic acid. As a result, the acetic acid product formed by the above-described low water carbonylation is frequently deficient with respect to the permanganate time owing to the presence therein of small proportions of residual impurities. Since a sufficient permanganate time is an important commercial test which the acid product must meet for many uses, the presence therein of such impurities that decrease permanganate time is objectionable [*Ullman's Encyclopedia of Industrial Chemistry*, "Acetic Acid", Volume A1, p 56, $5_{th}$ ed]. Of particular concern are certain carbonyl compounds and unsaturated carbonyl compounds, particularly acetaldehyde and its derivatives, crotonaldehyde and 2-ethyl crotonaldehyde (also referred to as unsaturated impurities). However other carbonyl compounds known also to effect the permanganate time are acetone, methyl ethyl ketone, butyraldehyde, and 2-ethyl butyraldehyde. Thus, these carbonyl impurities affect the commercial quality and acceptability of the product acetic acid. If the concentration of carbonyl impurities reaches only 10–15 ppm, the commercial value of the product acetic acid will certainly be negatively affected. As used herein the phrase "carbonyl" is intended to mean compounds which contain aldehyde or ketone functional groups which compounds may or may not possess unsaturation.

It is postulated in an article by Watson, *The Cativa™ Process for the Production of Acetic Acid*, Chem. Ind. (Dekker) (1998) 75 Catalysis of Organic Reactions, pp. 369–380, that enhanced rhodium catalyzed systems have increased standing levels of rhodium-acyl species which will form free acetaldehydes at a higher rate. The higher rate of acetaldehyde formation can lead to the increased production of permanganate reducing compounds.

The precise chemical pathway within the methanol carbonylation process that leads to the production of crotonaldehyde, 2-ethyl crotonaldehyde and other permanganate reducing compounds is not well understood. One prominent theory for the formation of the crotonaldehyde and 2-ethyl crotonaldehyde impurities in the methanol carbonylation process is that they result from aldol and cross-aldol condensation reactions starting with acetaldehyde. Because theoretically these impurities begin with acetaldehyde, many previously proposed methods of controlling carbonyl impurities have been directed towards removing acetaldehyde and acetaldehyde derived carbonyl impurities from the reaction system.

Conventional techniques used to remove acetaldehyde and carbonyl impurities have included treatment of acetic acid with oxidizers, ozone, water, methanol, amines, and the like. In addition, each of these techniques may or may not be combined with the distillation of the acetic acid. The most typical purification treatment involves a series of distillations of the product acetic acid. Likewise, it is known to remove carbonyl impurities from organic streams by treating the organic streams with an amine compound such as hydroxyl amine which reacts with the carbonyl compounds to form oximes followed by distillation to separate the purified organic product from the oxime reaction products. However, this method of treating the product acetic acid adds significant cost to the process.

There is disclosed in U.S. Pat. No. 5,625,095 to Miura et al. and PCT International Application No. PCT/US97/18711, Publication No. WO 98/17619 various methods of removing acetaldehydes and other impurities from a rhodium-catalyzed acetic acid production process. Generally, these methods involve extracting undesirable impurities from process streams to reduce acetaldehyde concentrations in the system.

The approaches described above have achieved a certain level of success in controlling carbonyl impurity concentrations in acetic acid produced by methanol carbonylation. Nonetheless, even with the use of these prior art removal methods, acetaldehyde and carbonyl impurities that derive from acetaldehyde, particularly, crotonaldehyde and 2-ethyl crotonaldehyde, continue to be a problem in product acetic acid produced by methanol carbonylation. Accordingly, a need remains for a method to control carbonyl impurities in product acetic acid produced by methanol carbonylation, particularly one which can be performed economically without adding to the impurities in the acetic acid or incorporating costly additional processing steps. It has been found that reduced levels of methyl iodide lead to improved purity profiles.

SUMMARY OF THE INVENTION

The improved method of the present invention unexpectedly reduces carbonyl impurities, particularly acetaldehyde and carbonyl impurities that derive from acetaldehyde. The inventive method focuses on reducing the formation of acetaldehyde, and thus the formation of its derivatives, crotonaldehyde and 2-ethyl crotonaldehyde, rather than focusing on removing acetaldehyde and carbonyl impurities that derive from acetaldehyde from the reaction system. Thus, the improved method of the present invention provides the benefits associated with a change in the chemistry of the carbonylation reaction to reduce the formation of acetaldehyde, crotonaldehyde, and 2-ethyl crotonaldehyde rather than additional equipment and process steps to remove them after they have formed.

Additional benefits also accrue from the method of the present invention. Operation of the methanol carbonylation process may still be carried out in a low water regime without sacrificing catalyst stability. The improved method does not require changes to the reaction or distillation equipment. The improved method decreases the demands presently placed on the distillation train of the plant, thus debottlenecking distillation and clearing the way for additional throughput.

In accordance with the present invention, an improved process for producing acetic acid by reacting methanol with carbon monoxide in a liquid reaction medium comprising a rhodium catalyst, a catalyst stabilizer/co-promoter which is an ionic iodide catalyst stabilizer/co-promoter, water, acetic acid, methyl iodide, and methyl acetate and subsequently recovering acetic acid from the resulting reaction product is provided. The ionic iodide will derive from any of many soluble salts which are useful. It will be recognized that it is the concentration of iodide ion in this catalyst system that is important and not the cation associated with the iodide, and that at a given molar concentration of iodide the nature of the cation is not as significant as the effect of the iodide concentration. Any metal salt, or any salt of any organic cation, can be used provided that the salt is sufficiently soluble in the reaction medium to provide the desired level of the iodide. Also the ionic iodide stabilizer/co-promoter may be in the form of a soluble salt of an alkali metal or alkaline earth metal salt or a quaternary ammonium or phosphonium salt that will generate an effective amount of iodide ion in the reaction solution. Iodide or acetate salts of lithium, sodium and potassium are particularly useful. The improvement comprises reducing contamination of the product acetic acid of carbonyl impurities by maintaining in the reaction medium during the course of the reaction (a) from about a finite (0.1 wt %) to less than about 14 wt % of water; (b) a salt soluble in the reaction medium at the reaction temperature in an amount operative to maintain a concentration of ionic iodide in the range of from about 2 to about 20 wt % effective as a catalyst stabilizer and co-promoter; (c) 5 wt % or less of methyl iodide; (d) from about 0.5 wt % to about 30 wt % of methyl acetate; and (e) a catalytically effective amount of rhodium.

Generally, the salt is a quaternary ammonium, phosphonium, or salt of a member of the group consisting of the metals of Group IA and IIA of the periodic table that provide an effective amount of ionic iodide. A comprehensive but non-exhaustive list appears in Table V of U.S. Pat. No. 5,026,908 to Smith et al., the disclosure of which is hereby incorporated by reference. Most preferably, the salt is lithium iodide or lithium acetate.

Typically, methyl iodide is maintained in the reaction medium in a concentration range of from about 1 to about 5 weight percent, with from about 2 to 4 weight percent usually being preferred. The water concentration in the reactor is preferably from about 1.0 to about 10 wt. percent of the reaction medium.

Rhodium is preferably present in the reaction medium at elevated levels, from about 500 to about 5000 parts per million by weight. From about 600 to about 2000 parts per million rhodium is more typical in the reaction medium, with from about 750 to about 1500 parts per million being preferred within that range.

DESCRIPTION OF SPECIFIC EMBODIMENTS

With the successes of previous improvements to the chemistry of the carbonylation reaction, particularly the reduction of the water concentration maintained during the reaction, we have learned that as the water concentration decreases, carbonyl impurities, namely acetaldehyde and carbonyl impurities that derive from acetaldehyde, particularly, crotonaldehyde and 2-ethyl crotonaldehyde, increase dramatically. Despite there being no definitively recognized chemical pathway within the carbonylation reaction which leads to the formation of acetaldehyde, crotonaldehyde, and 2-ethyl crotonaldehyde, we have learned that the formation of these impurities is a multi-faceted problem. Indeed, other factors may also affect their production. It has been found in accordance with the present invention that the rate of acetaldehyde generation is greatly influenced by methyl iodide concentration in the reactor.

We have discovered that by maintaining the methyl iodide concentration below levels previously recognized in the prior art, particularly at low water concentrations, the production of acetaldehyde and its derivatives, particularly crotonaldehyde and 2-ethyl crotonaldehyde, is dramatically reduced. In the prior art, methyl iodide has been maintained in concentrations at about 5 wt % or higher. By maintaining the methyl iodide concentration during the carbonylation reaction at about 5 wt % or less, quite unexpectedly, we have found the production of acetaldehyde, crotonaldehyde, and 2-ethyl crotonaldehyde, to be substantially reduced. Preferably methyl iodide is present at less than 5 wt %.

A typical homogeneous reaction system which is employed for the process of the present invention comprises (a) a liquid-phase carbonylation reactor, (b) a flasher, and (c) a methyl iodide-acetic acid splitter column. The carbonylation reactor is typically a stirred autoclave within which the reacting liquid contents are maintained automatically at a constant level. Into this reactor there are continuously introduced fresh methanol, sufficient water to maintain at least a finite (>50 ppm and preferably at least about 0.1 wt %) concentration of water in the reaction medium, recycled catalyst solution from the flasher base, and recycled methyl iodide, methyl acetate and water from the overhead of the methyl iodide-acetic acid splitter column. A distillation system can be employed to further process the condensed overhead stream from the flasher. The residue from the flasher is recirculated to the reactor. Carbon monoxide is continuously introduced into and thoroughly dispersed within the carbonylation reactor. A gaseous purge stream is vented from the head of the reactor to prevent buildup of gaseous by-product and to maintain a set carbon monoxide partial pressure at a given total reactor pressure. The temperature and pressure of the reactor are controlled by methods known in the art.

Crude liquid product is drawn off from the carbonylation reactor at a rate sufficient to maintain a constant level therein and is introduced to the flasher at a point intermediate between the top and bottom thereof. In the flasher the catalyst solution is withdrawn as a base stream predominantly acetic acid containing the rhodium catalyst and the iodide salt along with lesser quantities of methyl acetate, methyl iodide, and water, while the condensed overhead of the flasher comprises largely the crude product, acetic acid, along with methyl iodide, methyl acetate, and water. A portion of the carbon monoxide along with gaseous by-products such as methane, hydrogen, and carbon dioxide exits the top of the flasher.

The dry acetic acid (<1500 ppm water) product is drawn from the base of the methyl iodide-acetic acid splitter column (it can also be withdrawn as a side stream near the base) for final purification as desired by methods which are obvious to those skilled in the art and which are outside the scope of the present inventions. The overhead from the methyl iodide-acetic acid splitter, comprising mainly methyl iodide, methyl acetate and water, is recycled to the carbonylation reactor.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLES 1–3

Continuous methanol carbonylations were performed in a reaction system as described above, which includes a stirred reactor, a flasher, and a methyl iodide-acetic acid splitter column. Except for varying methyl iodide concentration the reaction conditions were repeated in each of the following examples to demonstrate the effect of reduced methyl iodide on acetaldehyde, crotonaldehyde and 2-ethyl crotonaldehyde formation. The reaction conditions are provided in Table 1.

Each run achieved steady state conditions before collecting impurity data by operating the reactor continuously to maintain constant target reaction compositions and conditions, as indicated in Table 1. Then, for at least 12 hours thereafter, data was collected and plots were maintained to indicate that the carbonylation reaction was in steady state mode.

The results of Examples 1–3 are provided in Table 1. With respect to Table 1, the values are mass balance data taken over at least a 12 hour period at steady state conditions. The results of Examples 1 and 3 each represent a single mass balance run. The results of Example 2 is an average of two mass balance operating periods.

Reactor acetaldehyde was sampled to show that even where acetaldehyde concentration in the reactor exceeds 500 ppm, operating at methyl iodide concentrations of about 5 wt % or less will reduce further acetaldehyde make rate, as compared to operating at higher methyl iodide concentrations.

The impurity make rates for acetaldehyde, crotonaldehyde, and 2-ethyl crotonaldehyde were measured from concentration values and flow rates from the crude acetic acid product stream of the reaction system. This stream is the condensed overhead from the flasher, that is, the feed stream to the methyl iodide-acetic acid splitter column. The impurity make rate results are reported as the space-time yield (STY) expressed as moles of carbonyl impurity produced per liter of hot unroused reaction solution per hour (mol/L-hr$\times 10^{-5}$).

As the data in Table 1 indicates, by maintaining the methyl iodide concentration during the carbonylation reaction at and preferably below 5 wt %, the acetaldehyde make rate decreased significantly, as did the make rate for unsaturates, crotonaldehyde and 2-ethyl crotonaldehyde. At a level of 2% methyl iodide in the reactor, the production of acetaldehyde is 2½ times less than at 6.7 wt % methyl iodide and the production of unsaturated impurities is more than 4 times less. This significant decrease in the acetaldehyde make rate is demonstrated in Table 1 also as the ratio of acetaldehyde make rate to acetic acid make rate in the various examples, as well as the ratio of unsaturates make rate to acetic acid make rate. In Table 1, "unsaturates" refers to the sum of crotonaldehyde, and 2-ethyl crotonaldehyde.

TABLE 1

Continuous Operation Results[1,2]

|  | 1 | 2 | 3 |
|---|---|---|---|
| REACTION CONDITIONS | | | |
| LiI (wt %) | 10 | 10 | 10 |
| Rh (ppm) | 630 | 610 | 620 |
| Water (wt %) | 4.0 | 4.1 | 3.9 |
| Methyl Acetate (wt %) | 3.0 | 2.7 | 3.0 |
| Methyl Iodide (wt %) | 2.0 | 3.5 | 6.7 |
| Hydrogen Partial Pressure (psia) | 12 | 11 | 11 |
| Acetic Acid STY (mol/L-hr) | 7 | 11 | 16 |
| REACTOR CONCENTRATION | | | |
| Acetaldehyde (ppm) | 540 | 610 | 660 |
| CONDENSED FLASHER OVERHEAD | | | |
| Acetaldehyde Make Rate (mol/L-hr $\times 10^{-5}$) | 8429 | 13672 | 20755 |
| Acetaldehyde STY: Acetic acid STY | 1204 | 1243 | 1297 |
| Unsaturates Make Rate (mol/L-hr $\times 10^{-5}$) | 9 | 32 | 38 |
| Unsaturates STY : Aetic acid STY | 1.3 | 2.9 | 2.4 |

Although the invention has been illustrated by the preceding examples, the invention is not to be construed as limited thereby; but rather, the invention encompasses the entirety of the subject matter disclosed. Various modifications and embodiments can be made without departing from the spirit and scope of the present invention.

[1]Acetaldehyde and unsaturate make rates (value $\times 10^{-5}$ mol/L-hr appears in Table I) are determined from condensed flasher overhead feed to methyl iodide—acetic acid splitter column
[2]Reaction temperature was 195° C. at 400 psig

What is claimed is:

1. In a process for producing acetic acid by reacting methanol with carbon monoxide in a liquid reaction medium comprising a catalytically effective amount of rhodium catalyst; from about 0.1 wt % to less than 14 wt % of water; acetic acid; a salt soluble in the reaction medium at the reaction temperature in an amount operative to maintain a concentration of ionic iodide in the range of from about 2 to about 20 wt % effective as a catalyst stabilizer and co-promoter, methyl iodide; from about 0.5 wt % to about 30 wt % of methyl acetate, methyl Iodide, and subsequently recovering acetic acid from the resulting reaction product, the improvement which comprises:

reducing contamination of the product acetic acid of carbonyl impurities by maintaining in the reaction medium during the course of the reaction less than about 4.5 wt % of methyl iodide.

2. The process of claim 1 wherein said salt is a quaternary ammonium or phosphonium salt or a salt of a member of the group consisting of the metals of Group IA and Group IIA of the periodic table.

3. The process of claim 2 wherein the salt is lithium iodide or lithium acetate.

4. The process according to claim 2, wherein the salt is a quaternary ammonium salt or a phosphonium iodide or acetate salt.

5. The process according to claim 2, wherein the salt is an iodide or acetate salt of sodium or potassium.

6. The process of claim 1 wherein methyl iodide is maintained in the reaction medium in a range of from about 1 wt % to less than about 4.5 wt %.

7. The process of claim 6, wherein methyl iodide is maintained in the reaction medium in a range from about 2 to about 4 wt %.

8. The process of claim 1 wherein water is maintained in the reaction medium in a range of from about 1.0 wt % to about 1.0 wt % water.

9. In a process for producing acetic acid by reacting methanol with carbon monoxide in a liquid reaction medium comprising a catalytically effective amount of rhodium; from about 0.1 wt % to less than 14 wt % of water; acetic acid; from about 2 wt % to about 20 wt % of a catalyst stabilizer and co-promoter selected from the group consisting of lithium iodide, lithium acetate, quaternary ammonium acetate salts, quaternary ammonium iodide salts, phosphonium iodide salts, phosphonium acetate salts, as well as other soluble Group IA and Group IIA salts, and mixtures thereof; methyl iodide; and from about 0.5 wt % to about 30 wt % of methyl acetate and subsequently recovering acetic acid from the resulting reaction product, the improvement which comprises:

reducing contamination of the product acetic acid of carbonyl impurities by maintaining in the reaction medium during the course of the reaction less than about 4.5 wt % methyl iodide.

10. The process of claim 9 wherein methyl iodide is maintained in the reaction medium in a range of from about 1 wt % to less than about 4.5 wt %.

11. The process of claim 10, wherein methyl iodide is maintained in the reaction medium in a range from about 2 to about 4 wt %.

12. The process of claim 10, wherein water is maintained in the reaction medium in a range of from about 1.0 wt % to about 10 wt % water.

13. In a process for producing acetic acid by reacting methanol with carbon monoxide in a liquid reaction medium comprising a catalytically effective amount of rhodium catalyst; from about 0.1 wt % to less than 14 wt % of water; acetic acid; a salt soluble in the reaction medium at the reaction temperature in an amount operative to maintain a concentration of ionic iodide in the range of from about 2 to about 20 wt % effective as a catalyst stabilizer and co-promoter; methyl iodide; and from about 0.5 wt % to about 30 wt % of methyl acetate and acetic acid and subsequently recovering acetic acid from the resulting reaction products the improvement which comprises:

reducing contamination of the product acetic acid of carbonyl impurities by maintaining in the reaction medium during the course of the reaction less than about 4.5 wt % methyl iodide and maintaining a rhodium concentration in the reaction medium of from about 500 to about 5000 parts per million rhodium by weight.

14. The process according to claim 13, wherein said rhodium concentration in said reaction medium is maintained in a range of from about 600 to about 2000 parts per million rhodium by weight.

15. The process according to claim 14, wherein said rhodium concentration in said reaction medium is maintained in a range of from about 750 to about 1500 parts per million by weight.

* * * * *